US012708305B2

(12) United States Patent
Stieglitz et al.

(10) Patent No.: US 12,708,305 B2
(45) Date of Patent: Aug. 18, 2026

(54) FLEXIBLE IMPLANTABLE ELECTRODE ARRANGEMENT AND PRODUCTION METHOD

(71) Applicant: Albert-Ludwigs-Universitat Freiburg, Freiburg (DE)

(72) Inventors: Thomas Stieglitz, Freiburg (DE); Calogero Gueli, Freiburg (DE); Maria Vomero, Freiburg (DE); Swati Sharma, Karlsruhe (DE)

(73) Assignee: Albert-Ludwigs-Universitat Freiburg, Freiburg (DE)

( * ) Notice: Subject to any disclaimer, the term of this patent is extended or adjusted under 35 U.S.C. 154(b) by 828 days.

(21) Appl. No.: 17/510,925

(22) Filed: Oct. 26, 2021

(65) Prior Publication Data

US 2022/0110568 A1 Apr. 14, 2022

Related U.S. Application Data

(63) Continuation of application No. PCT/EP2020/058480, filed on Mar. 26, 2020.

(30) Foreign Application Priority Data

Apr. 26, 2019 (DE) ......................... 102019205991.0

(51) Int. Cl.
*A61B 5/263* (2021.01)
*A61B 5/388* (2021.01)
(Continued)

(52) U.S. Cl.
CPC .............. *A61B 5/263* (2021.01); *A61B 5/388* (2021.01); *C01B 32/05* (2017.08); *C08L 79/08* (2013.01);
(Continued)

(58) Field of Classification Search
CPC ....... A61B 5/263; A61B 2562/04; D01F 9/22; H01B 1/04; C08L 79/08
See application file for complete search history.

(56) References Cited

U.S. PATENT DOCUMENTS

2012/0265025 A1* 10/2012 Hsiao .................. A61B 5/6801 600/300
2012/0301816 A1* 11/2012 Lee ...................... C01B 32/184 977/734
(Continued)

FOREIGN PATENT DOCUMENTS

CN 108744268 A 11/2018
DE 10 2005 033 831 A1 2/2007
(Continued)

OTHER PUBLICATIONS

Multiscale Carbon Structures Fabricated by Direct Micropatterning of Electrospun Mats of SU-8; Photoresist Nanofibers; Chandra S. Sharma, Ashutosh Sharma, and Marc Madou; Langmuir 2010 26 (4), 2218-2222; DOI: 10.1021/la904078r (Year: 2010).*
(Continued)

*Primary Examiner* — Adam Z Minchella
*Assistant Examiner* — Ashleigh Lauren Kern
(74) *Attorney, Agent, or Firm* — Barley Snyder

(57) ABSTRACT

A flexible implantable electrode arrangement includes an electrically insulating carrier structure of a first polymer material, an electrically conductive layer, and an electrically insulating cover layer of a second polymer material. The electrically conductive layer includes an electrically conductive carbon fiber layer. The electrically conductive layer integrally forms an implantable electrode, a conductor track connected to the implantable electrode, and a contact pad. The electrically insulating cover layer at least partially covers the electrically conductive layer.

17 Claims, 3 Drawing Sheets

(51) Int. Cl.

| | |
|---|---|
| ***C01B 32/05*** | (2017.01) |
| ***C08L 79/08*** | (2006.01) |
| ***C08L 83/04*** | (2006.01) |
| ***D01F 9/22*** | (2006.01) |
| ***D04H 1/4242*** | (2012.01) |
| ***D04H 1/728*** | (2012.01) |
| ***H01B 1/04*** | (2006.01) |
| ***H01B 3/30*** | (2006.01) |
| ***H01B 7/04*** | (2006.01) |

(52) U.S. Cl.
CPC ................ *C08L 83/04* (2013.01); *D01F 9/22* (2013.01); *D04H 1/4242* (2013.01); *D04H 1/728* (2013.01); *H01B 1/04* (2013.01); *H01B 7/048* (2013.01); *A61B 2562/0209* (2013.01); *A61B 2562/04* (2013.01); *A61B 2562/125* (2013.01); *A61B 2562/164* (2013.01); *C01P 2006/40* (2013.01); *C08L 2203/02* (2013.01); *D10B 2509/00* (2013.01); *H01B 3/30* (2013.01)

(56) References Cited

U.S. PATENT DOCUMENTS

| | | | | |
|---|---|---|---|---|
| 2014/0303470 | A1* | 10/2014 | Tsukada ................. | H01B 1/127 428/394 |
| 2016/0073920 | A1* | 3/2016 | Kassegne ............... | A61B 5/291 430/319 |
| 2018/0096801 | A1* | 4/2018 | Chen ...................... | H01G 11/26 |

FOREIGN PATENT DOCUMENTS

| | | | |
|---|---|---|---|
| KR | 1020180028101 | A | 3/2018 |
| WO | 2019046631 | A1 | 3/2019 |
| WO | 2020216573 | A1 | 10/2020 |

OTHER PUBLICATIONS

S. Kassegne, “Electrical impedance, electrochemistry, mechanical stiffness, and hardness tunability in glassy carbon MEMS μECoG electrodes”, “Microelectronic Engineering”, vol. 113, pp. 36-44, 2015.
M. Vomero, “Incorporation of Silicon Carbide and Diamond-Like Carbon as Adhesion Promoters Improves In Vitro and In Vivo Stability of Thin-Film Glassy Carbon Electrocorticography Arrays”, “Advanced Biosystems”, vol. 2, p. 170081, 2018.
German Office Action, App. No. 10 2019 205 991.0, dated Jan. 20, 2020, 3 pages.
International Search Report and English translation, Intl App No. PCT/EP2020/058480, dated Jun. 3, 2020, 11 pages.
Surabhi Nimbalkar, et al., “Ultra-Capacitive Carbon Neutral Probe Allows Simultaneous Long-Term Electrical Stimulations and High-Resolution Neurotransmitter Detection”, Scientific Reports, vol. 8, No. 1, published May 3, 2018 DOI: 10.1038/s41598-018-25198-x, 14 pages.
Abstract of CN 108744268, dated Nov. 6, 2018, 1 page.
Abstract of DE 102005033831, dated Feb. 1, 2007, 1 page.

* cited by examiner 104
102

106
104
102

106
104
102

108
106
104
102

108
106
104
102

106
104
102

110
106
104
102

106
110
112
104
102

106
110
112
104
100

114

106

106
104
102

106
104
102

110
106
104
102

110
112
104
102

110
112
104
106
100

FLEXIBLE IMPLANTABLE ELECTRODE ARRANGEMENT AND PRODUCTION METHOD

CROSS-REFERENCE TO RELATED APPLICATIONS

This application is a continuation of PCT International Application No. PCT/EP2020/058480, filed on Mar. 26, 2020, which claims priority under 35 U.S.C. § 119 to German Patent Application No. 102019205991.0, filed on Apr. 26, 2019.

FIELD OF THE INVENTION

The present invention relates to flexible implantable electrode arrangements, e.g. electrode arrays, and to an associated production method.

BACKGROUND

Recent research and development in the field of neural engineering has resulted in a plurality of active implantable medical devices (AIMD) that can be used for a wide range of applications. They typically consist of a housing that contains control electronics and a battery, implantable electrodes (or electrode arrays), and cables for establishing electrical contact with the electrodes and the electronics. The electrodes are used for the electrical stimulation of cells or for recording physiological signals.

Neural electrodes therefore serve as an interface between the biological and the technical system, where their task is substantially recording and/or exciting neural signals. When neural electrodes are used in AIMD, they play a key role in restoring and maintaining bodily functions in patients with physical disabilities. Such electrodes have an electrically conductive material for the contact regions and the connection points as well as a substrate material which insulates the electrically conductive materials. Crucial prerequisites for the success of implantable medical devices are, firstly, an advantageous tissue-electrode interaction and, secondly, adequate biostability. For this reason, the mechanical flexibility of the electrode is an essential aspect in the design of neural probes for obtaining structural biocompatibility and thereby reducing the foreign object reaction and increasing the service life of the implant.

Electrically conductive carbon materials meet the requirements in terms of biostability as well as in terms of the recording and stimulation abilities, but they typically do not have the ability to follow curved trajectories without fracturing because they are hard and brittle. Therefore, carbon material is used nowadays only at the contact points of the electrode within a comparatively small area, while the conductor tracks are produced from thin metal films. Such electrodes are shown, for example, in the publication S. Kassegne, “Electrical impedance, electrochemistry, mechanical stiffness, and hardness tunability in glassy carbon MEMS μECoG electrodes”, “Microelectronic Engineering”, vol. 113, pages 36-44, 2015. In some cases, adhesion promoters are also employed between the carbon material and the metal (see M. Vomero, “Incorporation of Silicon Carbide and Diamond-Like Carbon as Adhesion Promoters Improves In Vitro and In Vivo Stability of Thin-Film Glassy Carbon Electrocorticography Arrays”, “Advanced Biosystems”, vol. 2, page 170081, 2018).

However, known arrangements have at least one interface between the carbon electrodes and the metal, which easily leads to failures. With a larger number of interfaces, there is a risk of failure at each of these interfaces.

When carbon material is used, there is basically the problem that the carbon material is inert and therefore has difficulties to form bonds with any type of surrounding material. This is disadvantageous primarily for the adhesion to a substrate and the electrical connection to a metallic conductor track or a metallic contact pad.

Furthermore, carbon material is hard and brittle. Deformations can therefore lead to the fracture of the structures so that both the flexibility of the electrode as well as the absolute size of the structures that can be implemented are limited.

If adhesion promoters are used between the carbon material and the metals connected thereto, then this again increases the number of interfaces and thereby leads to an increased probability of failure.

SUMMARY

A flexible implantable electrode arrangement includes an electrically insulating carrier structure of a first polymer material, an electrically conductive layer, and an electrically insulating cover layer of a second polymer material. The electrically conductive layer includes an electrically conductive carbon fiber layer. The electrically conductive layer integrally forms an implantable electrode, a conductor track connected to the implantable electrode, and a contact pad. The electrically insulating cover layer at least partially covers the electrically conductive layer.

BRIEF DESCRIPTION OF THE DRAWINGS

The invention will now be described by way of example with reference to the accompanying Figures, of which.

DETAILED DESCRIPTION OF THE EMBODIMENT(S)

Figure 1:
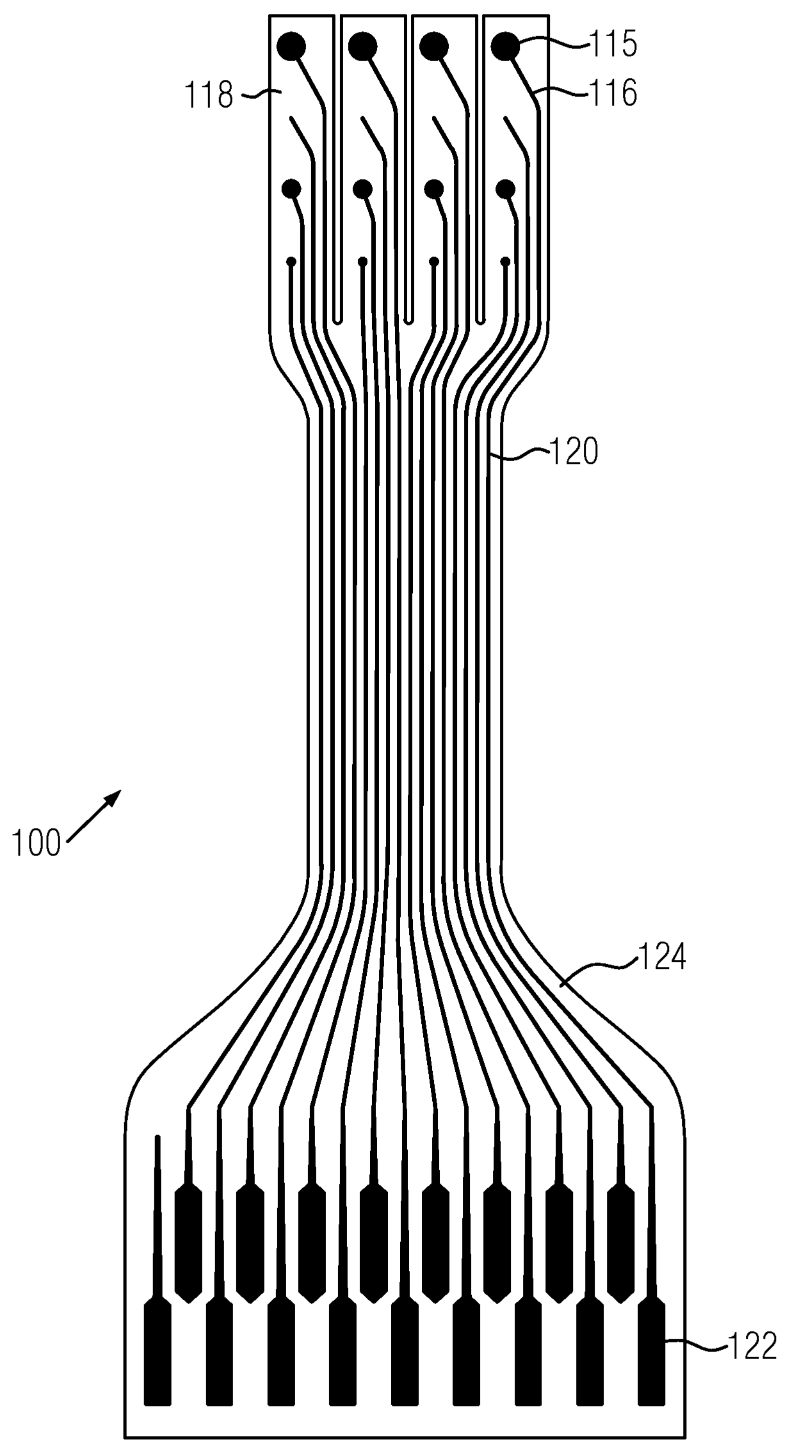
FIG. 1 is a schematic top view of an electrode arrangement according to an embodiment.

For a better understanding of the present invention, it shall be explained in more detail with reference to the embodiments shown in the figures. Same parts are provided with the same reference characters and the same component names. Furthermore, some features or combinations of features from the different embodiments shown and described can in themselves represent solutions that are independent according to the invention.

The following terms and definitions are used hereafter.

In the context of the present invention, the term "flexible" means that a layer or a substrate can be bent and, in particular, can be deformed within certain limits without fracturing or at least without losing the desired electrical and mechanical properties.

The term "electrically conductive" is understood hereafter to mean that a material is able to conduct electrical current and is suitable for the formation of electrodes. In addition to conductivity, which, for example, is exhibited by metals, the conductivity of semiconducting material is also intended to be included in the context of the present invention.

The term "graphitic" is understood to mean a carbon material that has $sp^2$-covalently hexagonally bonded carbon atoms that form fixed planes, wherein the fixed planes are arranged in any desired manner relative to one another to form the carbon fibers.

The present invention shall be explained in more detail hereafter with reference to the figures, and in particular first with reference to the schematic sectional representation of FIG. 1. It is to be noted that the size ratios in all of the figures and in particular the layer thickness ratios are not necessarily shown true to scale.

FIG. 1 shows an embodiment of an electrode arrangement 100 in a top view which comprises an array of sixteen individual electrodes 116 in the shown embodiment. Four (differently configured) individual electrodes 116 each are combined to form a group of electrodes which form a sensor 118. Depending on the shape of the electrode, stimulation signals can be supplied into a nerve cell and measurement signals can be tapped from the nerve cell via such a sensor 118.

According to the invention, individual electrodes 116 are each formed integrally with a conductor track 120, as shown in FIG. 1. Furthermore, each conductor track 120 is in turn connected integrally to a contact surface 122 (also referred to hereafter as a contact pad). This eliminates the need for two interfaces that could otherwise cause failures.

According to the present invention, all electrically conductive structures are produced from carbon fiber material, as shall be explained in detail with reference to FIGS. 2 and 3. For electrical insulation, conductive structures 116, 118, 120, 122 are embedded in electrically insulating polymer material 124 shown in FIG. 1. The polymer envelopment is provided with respective openings at the points at which the electrically conductive material must be accessible, namely in active regions 115 of electrodes 116 and at contact pads 122 (see FIGS. 2 and 3). The polymer material can be formed, for example, by polyimide.

It was shown experimentally that electrode arrangement 100 according to the invention can be produced in a highly miniaturized manner (e.g. with critical dimensions of approximately 12.5 μm). The conductive structures 116, 118, 120, 122 are highly flexible and mechanically stable and it was possible to demonstrate excellent mechanical anchoring of the carbon fiber layer to the electrically insulating material 124. The carbon fiber structures showed no measurable decrease in electrical conductivity even after 100,000 cycles of bending stress. In this way, the present invention provides a completely metal-free and extremely flexible, both mechanically as well as electrically extremely stable electrode arrangement 100.

In summary, the electrode arrangement 100 according to the present invention provides the following advantages:

- no additional interfaces between the active region 115 of the electrodes 116 and the connection region to external components,
- strong mechanical integration of the conductive structures 116, 118, 120, 122 into the polymer 124,
- mechanical flexibility that is required for structural biocompatibility,
- high mechanical and electrical stability of the electrically conductive material,
- long service life of the electrode due to the increased stability.

FIGS. 2A to 2I schematically show the production process of a flexible implantable electrode arrangement 100 according to the invention.

Figures 2A, 2B, 2C, 2D, 2E, 2F, 2G, 2H, 2I:
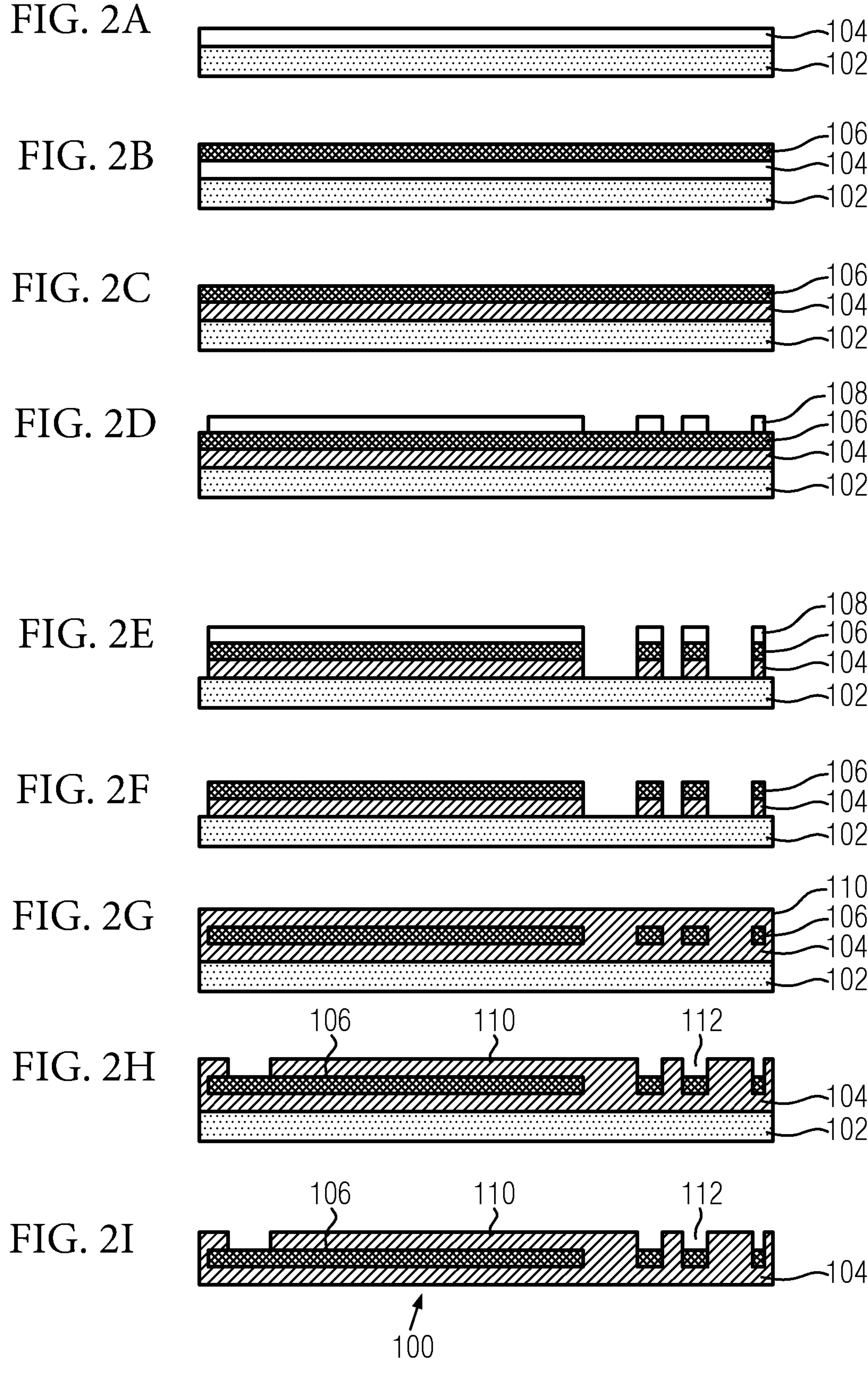
FIG. 2A schematic sectional side view of a first step of a method of producing an electrode arrangement according to an embodiment.
FIG. 2B is a schematic sectional side view of a second step of the method of FIG. 2A.
FIG. 2C is a schematic sectional side view of a third step of the method of FIG. 2A.
FIG. 2D is a schematic sectional side view of a fourth step of the method of FIG. 2A.
FIG. 2E is a schematic sectional side view of a fifth step of the method of FIG. 2A.
FIG. 2F is a schematic sectional side view of a sixth step of the method of FIG. 2A.
FIG. 2G is a schematic sectional side view of a seventh step of the method of FIG. 2A.
FIG. 2H is a schematic sectional side view of a eighth step of the method of FIG. 2A.
FIG. 2I is a schematic sectional side view of a ninth step of the method of FIG. 2A.

FIG. 2A shows a substrate 102 as starting material, for example a silicon or glass wafer, onto which a future carrier structure 104 is applied, for example, a polyimide layer. Of course, other polymers that form this first polymer layer 104 can also be used, as described below. The polyimide layer 104 can be deposited onto substrate 102 in the form of a liquid precursor that has not cured or has only cured in part, for example, by use of a spin-on process. If polyimide is used, then a polyimide precursor is employed as a preliminary stage which is first imidized in a post-curing step above 200° C. and then cyclized in a post-curing step at 400° C. subject to nitrogen. The fully cyclized polyimide layer is temperature-stable up to almost 500° C. The polyimide precursor can furthermore be provided with photo-crosslinkable admixtures so that the polyimide layer 104 that has not yet cyclized can be photo-structured. Disaggregated polyimide layer 104, in an embodiment, is first subjected to a drying step in which solvents are expelled, but without causing complete cyclization, prior to the carbon fiber layer being applied.

In the next step, which is shown in FIG. 2B, a carbon fiber layer 106 that has not yet been structured is deposited on carrier structure 104. In various embodiments, the carbon fiber layer 106 is a woven fabric, knitted fabric, or nonwoven fabric. For example, such nonwoven fabric can be produced in an electrospinning process. Electrospinning can produce fibers having diameters ranging from nanometers to micrometers. Nonwovens of ultra-thin fibers combine their relatively large specific surface and macroporous properties, i.e. pore sizes of several micrometers. This makes them attractive for any application in which very good diffusion properties are required within a matrix having a large specific surface area. Being cohesive material, they are self-supporting and macroscopically easy to handle. The electrospinning process is based on the fact that the surface tension of a drop of liquid can be overcome by applying a high electrical voltage, and a fine jet of liquid then emerges from the drop. With low-molecular liquids, this jet breaks up into many very small, highly charged droplets. When using polymeric substances, fibers are created that are deposited on the counter electrode as a nonwoven material. The fine electrode structures are then produced directly on the carrier material 104 so that the structures are supported by the carrier and protected from damage.

The layer sequence is subsequently subjected to a thermal treatment step in which carrier structure 104 is converted to the fully cyclized polyimide form. This is indicated by the hatching in FIG. 2C. As is well known, polyimide cures at around 400° C. Of course, temperature step profiles can also be performed during this post-curing process. This post-curing step leads to carbon fibers 106 being embedded in part in the upper regions of carrier structure 104.

Carbon fiber layer 106 must be structured in order to form an electrode arrangement, for example, an array of electrodes, and electrical lines and contact pads. FIG. 2D schematically illustrates that a mask 108 is applied for this purpose. Mask 108 leaves all the areas free in which electrically conductive carbon fiber layer 106 is to be removed. For example, this mask 108 can be structured with the aid of photolithography, as is customary in semiconductor technology.

In the next step, shown in FIG. 2E, the material is removed in a wet or dry etching step from the areas not protected by mask 108. For example, reactive ion beam etching (ME) can advantageously be used. In this case, not only carbon fiber layer 106 but also at least a part of carrier structure 104 can be removed at the points not covered by mask 108. This is advantageous for the subsequent bonding of a cover layer. Mask 108 is thereafter removed again, as shown in FIG. 2F.

However, it is clear to a person skilled in the art that direct structuring of the carbon fiber layer 106, i.e. without a mask 108, e.g. by way of a laser structuring or laser ablation process, can be used to produce the conductive structures.

In any case, the result of the structuring process is the arrangement shown in FIG. 2F in which the electrode arrangement 100, for example, an array of electrodes, and electrical lines and contact pads are formed by the carbon fiber layer 106 on carrier structure 104.

In the next step, which is illustrated in FIG. 2G, a cover layer 110 comprising a second polymer material is applied over the entire area. Cover layer 110 connects to carrier structure 104 so that structured carbon fiber layer 106 is completely enveloped by first and second polymer material 104, 110. This ensures high mechanical stability and reliable electrical insulation of carbon fiber layer 106. In an embodiment, the second polymer forming cover layer 110 can again be polyimide which is spun on in the form of a precursor material and then cured in a post-curing step. The carbon fiber material 106 is advantageously open-pored so that the first and/or second polymer material can penetrate at least in part into the carbon fiber layer 106. As a result, a firm bond can be obtained, firstly, to the carbon fiber layer 106 and, secondly, to the carrier structure 104 disposed therebeneath.

In other embodiments, the cover layer 100 can be deposited by atomization, or spray coating, by vapor deposition or in a potting process, depending on the material respectively employed.

The electrically conductive structures of carbon fiber layer 106 must be accessible substantially at two interfaces and therefore freed from cover layer 110. Firstly, the active regions of the electrode must be able to contact the biological environment, and secondly, the contact pads must be electrically contactable to connect the electrical conductor tracks to other electronic components for the supply and/or read-out of the electrodes.

FIG. 2H shows the arrangement after corresponding openings 112 have been introduced into cover layer 110. For the introduction of openings 112, e.g. further photolithography with a mask can be carried out, or direct structuring by way of laser ablation can be done. Furthermore, photo-structurable resin, e.g. a photo-structurable polyimide, can be used as the second polymer material 110.

In the last step, the electrode arrangement is separated from substrate 102 which supports it during the production method, as is shown in FIG. 2I. This can be done either by etching away substrate 102 or by lifting off electrode arrangement 100.

A wide variety of plastic materials can be used for the first and the second polymer material 104, 110. For example, the first and/or the second polymer material 104, 110 comprise polyimide, PI, polyethylene terephthalate, PET, polyethylene, PE, polycarbonate, PC, polyvinyl chloride, PVC, polyamide, PA, polytetrafluoroethylene, PTFE, polymethyl methacrylate, PMMA, polyether ether ketone, PEEK, polysulfone, PSU, Polyp-xylylene), polydimethylsiloxane, PDMS, and/or polypropylene, PP. The carrier structure 104 and the cover layer 110 can be made from the same material or from different materials. Polyimide has several advantages: Firstly, when fully crosslinked, it is particularly inert and chemically stable. Secondly, it can be spun on in the form of a liquid precursor and additionally has a second, solid, but not yet completely cured preliminary stage, in which, e.g. the adhesion of the carbon fiber layer 106 and/or the subsequent polymer layer 110 is improved. Finally, photo-structurable polyimide resin systems exist which allow the contact pads to be opened in a simple manner e.g. for the production of the cover layer 110.

A modified production method for the electrode arrangement 100 according to the invention shall be explained hereafter with reference to FIG. 3. It is clear to a person skilled in the art that individual features of the two methods can be combined with one another as desired and that some of the individual process steps can also be conducted in a different sequence. In particular, it is also possible to reverse the layer sequence of cover and carrier layers in such a way that first a layer with the contact openings is produced on the substrate, the carbon fiber layer is applied thereafter and structured, and finally the carrier structure is deposited and optionally likewise structured. This procedure has the advantage that openings on both sides for rear-side contacts are possible.

Figures 3A, 3B, 3C, 3D, 3E, 3F, 3G:
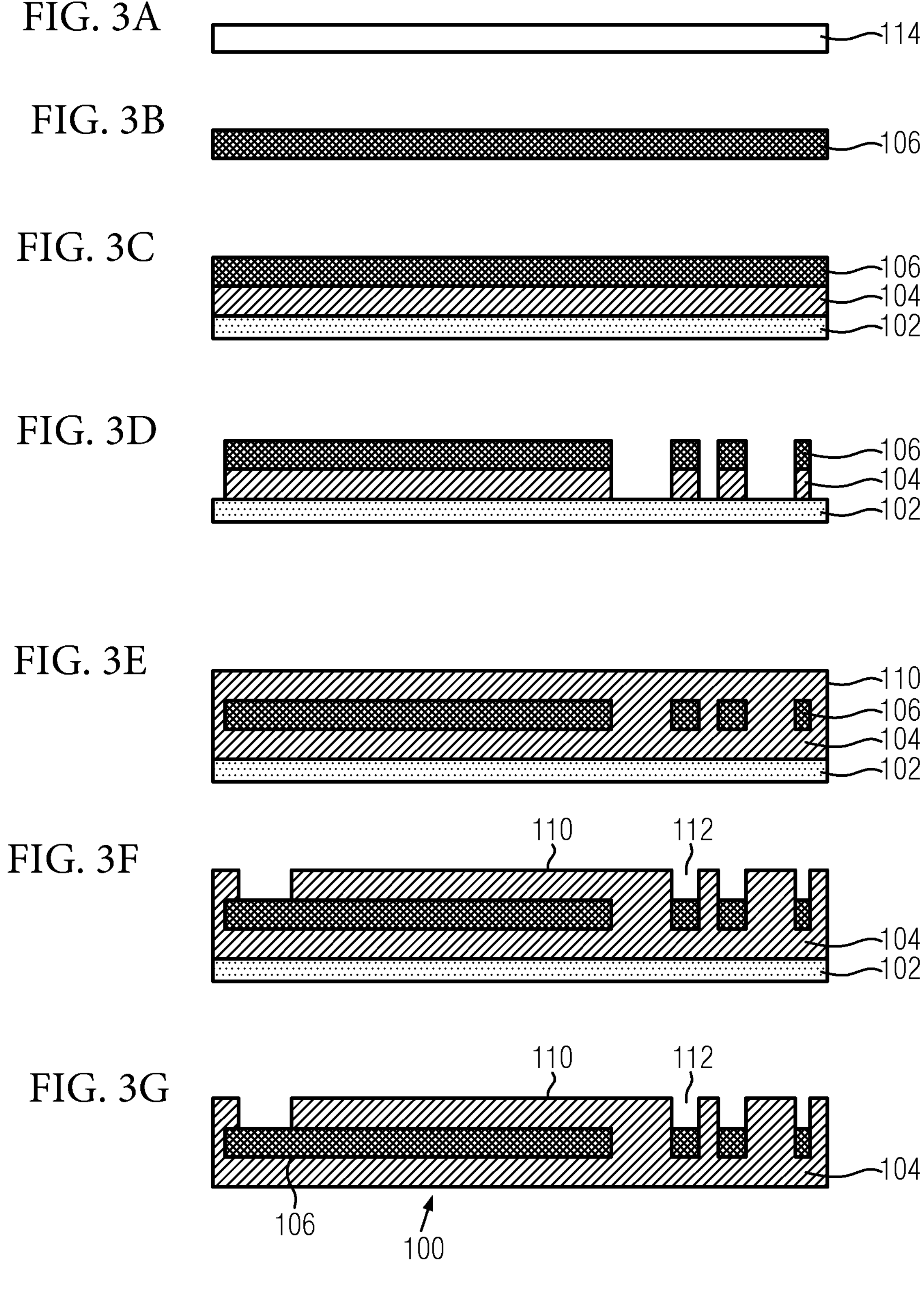
FIG. 3A schematic sectional side view of a first step of a method of producing an electrode arrangement according to another embodiment.
FIG. 3B is a schematic sectional side view of a second step of the method of FIG. 3A.
FIG. 3C is a schematic sectional side view of a third step of the method of FIG. 3A.
FIG. 3D is a schematic sectional side view of a fourth step of the method of FIG. 3A.
FIG. 3E is a schematic sectional side view of a fifth step of the method of FIG. 3A.
FIG. 3F is a schematic sectional side view of a sixth step of the method of FIG. 3A.
FIG. 3G is a schematic sectional side view of a seventh step of the method of FIG. 3A.

As shown in FIG. 3A, a polyacrylonitrile (PAN) fiber mat 114 can be produced e.g. by way of an electrospinning process, in a first step in the production of an electrode arrangement 100. A 10% (weight/volume) solution of PAN in dimethylformamide (DMF) is there spun onto a silicon substrate at 10 kV and a polymer flow rate of 0.6 ml/h. The PAN fiber mat can then be stabilized in a dry heating chamber for 120 minutes at 220° C. in an atmosphere containing oxygen. PAN fiber mat 114 shown in FIG. 3A is thus obtained.

The stabilized PAN fiber mat is then pyrolyzed at 940° C. subject to a nitrogen atmosphere. A heating ramp of 5° C./min and a holding time of 60 min can be provided. FIG. 3B shows resulting carbon fiber mat 106. Therefore, the carbon fiber material 106 can have a graphitic structure at least in part, i.e. have $sp^2$-covalently hexagonally bonded carbon atoms which are arranged in mutually twisted and folded planes. The individual planes are only bonded by van der Waals forces. However, it is clear to a person skilled in the art that all other common methods in which a carbon fiber layer 106 with sufficient electrical conductivity is produced can also be used within the scope of the present invention. For example, cellulose or pitch can also serve as starting materials.

In the subsequent step, shown in FIG. 3C, a layer of a polyimide precursor having a thickness of 2 μm is spun onto a silicon substrate 102 and dried on at 90° for 3 minutes. A second polyimide layer is spun onto the first polyimide layer (not visible in the figure) in order to thus form carrier structure 104. A carbon fiber mat 106 is placed onto the surface of the polyimide layer 104 that has not yet cured and the arrangement shown in FIG. 3C is then dried at 90° C. for 3 minutes (soft-curing). The final cyclization then takes place at 450° C.

In order to shape the conductive structures in carbon layer 106, respective structuring is carried out in the next step, shown in FIG. 3D, by way of a reactive ion etching step (RIE) using oxygen plasma. The regions that are not to be removed are covered by way of a phototechnically structured metallization, and the metal mask is subsequently removed again.

As shown in FIG. 3E, a polyimide layer, for example, 4 μm thick, is spun on as cover layer 110 and fully cyclized. Prior to the application of cover layer 110, the surface of the arrangement to be coated shown in FIG. 3D can optionally be activated with the aid of oxygen plasma (for example 80 W for 30 seconds). This improves the adhesion of cover layer 110 to the substrate.

In order to define the outer contours of the electrode arrangement, an RIE etching step can be carried out again using a photo-technically produced mask. As shown in FIG. 3F, openings 112 for the active regions and the contact pads are also introduced with the aid of a further RIE etching step Finally, the individual electrode arrangements 100 are detached from silicon substrate 102, as shown in FIG. 3G.

In summary, the present invention provides a method for the production of electrode arrangements 100 comprising pyrolyzed carbon fiber material 106 for forming the conductive structures 116, 118, 120, 122 embedded in a polyimide material 124. The carbon fiber structures proved to be highly flexible and electrically as well as mechanically stable. Even if individual fibers break when bent, the electrical conductivity is maintained unchanged due to the mechanical embedding of the carbon fiber layer 106 into the polymer material 124. The adhesion of the individual layers to one another can also be ensured over long periods of time and in aggressive environments due to the specific process control.

Since the carbon fiber material 106 is applied as a fiber mat, it can also be used to form larger structures, such as contact pads, without fracturing under deformation and without requiring any additional interface between the active electrode region and the connection to external devices. Such an integrally formed arrangement with the carbon fiber layer 106, which includes the at least one electrode structure as well as the electrical leads and the contact pads required for contacting, has the advantage of being very efficient to manufacture. In addition, there are no transitions or interfaces between the electrode and the leads and between the leads and the contact surface so that the electrical properties and long-term stability can be significantly improved over multi-part arrangements. This integration results in a high mechanical stability and high stability with electrical stimulation.

In addition, the use of carbon fibers 106 means that the electrically conductive structures 116, 118, 120, 122 are embedded in the insulating polymer material 124 and penetrated by the latter. For the reason that graphitic carbon material is very resistant to corrosion, electrode arrangements with excellent stability and durability can furthermore be produced. Therefore, implanted electrodes have to be replaced less frequently, which is advantageous for the user. Furthermore, the carbon fiber material 106 can be used to enable a multimodal platform for the simultaneous recording, stimulation, and detection of chemical substances. The flexible implantable electrode arrangement 100 can be produced are safely and reliably, but can nevertheless be produced inexpensively.

What is claimed is:

1. A flexible implantable electrode arrangement, comprising:
- an electrically insulating carrier structure comprising a first polymer material;
- an electrically conductive layer comprising an electrically conductive carbon fiber layer, the electrically conductive layer integrally forms an implantable electrode, a conductor track connected to the implantable electrode, and a contact pad, the electrically conductive carbon fiber layer is a structured mat made from a woven fabric, knitted fabric, or non-woven fabric, the structured mat is structured to remove a plurality of portions of the electrically conductive carbon fiber layer to form the implantable electrode, the conductor track, and the contact pad in a single piece of the electrically conductive carbon fiber layer with no interface between the implantable electrode and the conductor track; and
- an electrically insulating cover layer comprising a second polymer material, the electrically insulating cover layer at least partially covering the electrically conductive layer.

2. The flexible implantable electrode arrangement of claim 1, wherein the first polymer material and/or the second polymer material comprise at least one of: polyimide, polyethylene terephthalate, polyethylene, polycarbonate, polyvinyl chloride, polyamide, polytetrafluoroethylene, polymethyl methacrylate, polyether ether ketone, polysulfone, Poly(p-xylylene), polydimethylsiloxane, and/or polypropylene.

3. The flexible implantable electrode arrangement of claim 1, wherein the electrically conductive carbon fiber layer is produced from a pyrolyzed polymer material.

4. The flexible implantable electrode arrangement of claim 1, wherein the electrically insulating cover layer and/or the electrically insulating carrier structure at least partially penetrates into the electrically conductive carbon fiber layer.

5. A method for producing an implantable electrode arrangement, comprising:
- providing an electrically insulating carrier structure comprising a first polymer material;
- applying an electrically conductive layer comprising an electrically conductive carbon fiber layer on the electrically insulating carrier structure, the electrically conductive layer integrally forms an implantable electrode, a conductor track connected to the implantable electrode, and a contact pad, the electrically conductive carbon fiber layer is a carbon fiber mat made from a woven fabric, knitted fabric, or non-woven fabric;
- structuring the carbon fiber mat into a structured mat by removing a plurality of portions of the electrically conductive carbon fiber layer to form the implantable electrode, the conductor track, and the contact pad in a single piece of the electrically conductive carbon fiber layer with no interface between the implantable electrode and the conductor track; and applying an electrically insulating cover layer to at least partially cover the electrically conductive layer, the electrically insulating cover layer comprises a second polymer material.

6. The method of claim 5, wherein the electrically insulating carrier structure is provided on a substrate in a form of a precursor of the first polymer material that has not cured or has only cured in part.

7. The method of claim 5, wherein the carbon fiber mat is structured using an etching mask layer by wet etching or dry etching.

8. The method of claim 5, wherein the carbon fiber mat is structured without a mask directly by laser ablation.

9. The method of claim 5, wherein the carbon fiber mat is produced by pyrolysis of a polymer.

10. The method of claim 9, wherein the polymer is polyacrylonitrile.

11. The method of claim 5, wherein the electrically insulating cover layer is applied on the electrically conductive carbon fiber layer in a form of a precursor of the first polymer material that has not cured or has only cured in part.

12. The method of claim 5, wherein the electrically insulating cover layer is deposited in a spin-on process, by atomization, by spray coating, by vapor deposition, or in a potting process.

13. The method of claim 5, wherein the first polymer material and/or the second polymer material comprise polyimide and/or polydimethylsiloxane.

14. The method of claim 5, wherein the carbon fiber mat is produced by an electrospinning process.

15. The method of claim 5, further comprising activating the first polymer material by an oxygen plasma prior to applying the second polymer material.

16. The flexible implantable electrode arrangement of claim 1, wherein the structured mat is a planar layer consisting of carbon.

17. The method of claim 5, wherein the structured mat is a planar layer consisting of carbon.

* * * * *